United States Patent [19]

Priegnitz et al.

[11] Patent Number: 4,480,129
[45] Date of Patent: Oct. 30, 1984

[54] PROCESS FOR SEPARATING ISOMERS OF TOLUIDINE

[75] Inventors: James W. Priegnitz, Elgin; Hermann A. Zinnen, Evanston, both of Ill.

[73] Assignee: UOP Inc., Des Plaines, Ill.

[21] Appl. No.: 537,123

[22] Filed: Sep. 29, 1983

[51] Int. Cl.$^3$ .............................................. C07C 85/26
[52] U.S. Cl. .................................................. 564/424
[58] Field of Search ........................................ 564/424

[56] References Cited

U.S. PATENT DOCUMENTS

| | | | |
|---|---|---|---|
| 2,985,589 | 5/1961 | Broughton et al. | 210/34 |
| 3,069,470 | 12/1962 | Fleck et al. | 260/582 |
| 3,114,782 | 12/1963 | Fleck et al. | 260/674 |
| 3,201,491 | 8/1965 | Stine et al. | 260/676 |
| 3,265,750 | 8/1966 | Peck et al. | 260/666 |
| 3,510,423 | 4/1968 | Neuzil et al. | 208/310 |
| 3,558,730 | 1/1971 | Neuzil | 260/674 |
| 3,558,732 | 1/1971 | Neuzil | 260/674 |
| 3,626,020 | 3/1971 | Neuzil | 260/674 SA |
| 3,663,638 | 5/1972 | Neuzil | 260/674 SA |
| 3,668,267 | 6/1972 | Hedge | 260/674 SA |
| 3,734,974 | 5/1973 | Neuzil | 260/674 SA |
| 3,864,416 | 2/1975 | Campbell et al. | 260/674 A |
| 4,371,721 | 2/1983 | Wu | 564/424 X |

Primary Examiner—Paul F. Shaver
Attorney, Agent, or Firm—James R. Hoatson, Jr.; Louis A. Morris; William H. Page, II

[57] ABSTRACT

This invention comprises a process for separating p-toluidine from a feed mixture comprising p-toluidine and o- or m-toluidine, which process comprises contacting the mixture at adsorption conditions with an adsorbent comprising an X or Y-type zeolite cation exchanged with a cation in the group Fe, Mn, Co, Ni or Zn, thereby selectively adsorbing the p-toluidine. The remainder of the feed mixture is removed from the adsorbent and the p-toluidine is recovered by desorption at desorption conditions with a desorbent material comprising aniline or an alkyl amine excluding alkyl amines having eight or more carbon atoms per molecule when the adsorbent comprises an X-type zeolite.

6 Claims, No Drawings

PROCESS FOR SEPARATING ISOMERS OF TOLUIDINE

BACKGROUND OF THE INVENTION

1. Field of the Invention

The field of art to which this invention pertains is the solid bed asorptive separation of isomeric toluidines. More specifically, the invention relates to a process for separating para-toluidine from the other toluidine isomers by employing a solid bed absorption system.

2. Background Information

It is well known in the separation art that certain crystalline aluminosilicates can be used to separate hydrocarbon types from mixtures thereof. As a few examples, a separation process disclosed in U.S. Pat. Nos. 2,985,589 and 3,201,491 uses a Type A zeolite to separate normal paraffins from branched chain paraffins, and processes described in U.S. Pat. Nos. 3,265,750 and 3,510,423 use type X or type Y zeolites to separate olefinic hydrocarbons from paraffinic hydrocarbons. In addition to their use in processes for separating hydrocarbon types, X and Y zeolites have been employed in processes to separate individual hydrocarbon isomers. As a few examples, adsorbents comprising X and Y zeolites are used in the process described in U.S. Pat. No. 3,114,782 to separate alkyl-trisubstituted benzene isomers; in the process described in U.S. Pat. No. 3,864,416 to separate alkyl-tetrasubstituted monocyclic aromatic isomers; and in the process described in U.S. Pat. No. 3,668,267 to separate specific alkyl-substituted naphthalenes. Because of the commercial importance of para-xylene, perhaps the more well-known and extensively used hydrocarbon isomer separation processes are those for separating para-xylene from a mixture of $C_8$ aromatics. In processes described in U.S. Pat. Nos. 3,558,730; 3,558,732; 3,626,020; 3,663,638; and 3,734,974, for example, adsorbents comprising particular zeolites are used to separate para-xylene from feed mixtures comprising para-xylene and at least one other xylene isomer by selectively adsorbing para-xylene over the other xylene isomers.

In contrast, this invention relates to the separation of non-hydrocarbons and more specifically to the separation of the isomers of toluidine. Substantial uses of toluidine are in dyes or dye intermediates, e.g., o-Toluidine is a precursor of azo dyes such as Acid Red 24, Solvent Yellow 3, Solvent Red 26 and Direct Red 62, while p-Toluidine is a precursor of Basic Red 9, Acid Green 25 and Acid Blue 78.

It is known from U.S. Pat. No. 3,069,470 to Fleck et al., to use type X zeolites for the separation of isomers of toluidine. The type X zeolite was found to be least selective for the para-isomer. Fleck et al. specifically states (column 2, lines 21–23), with regard to its process, that of three toluidine isomers, meta toluidine is preferentially adsorbed and paratoluidine is the least readily adsorbed. In Japanese Patent Application No. 56905/79, publicly disclosed on Nov. 20, 1980, it is disclosed that a solid adsorbent containing titanium oxide will selectively adsorb the p-isomer of toluidine.

We have discovered, contrary to the express teachings of the art, particularly Fleck et al., that certain cation exchanged X and Y zeolites are selective for para-toluidine over the other isomers, when used with the appropriate desorbent material.

SUMMARY OF THE INVENTION

In brief summary, the invention is, in one embodiment, a process for separating p-toluidine from a mixture comprising p-toluidine and o-toluidine and/or m-toluidine. The process comprises contacting the mixture at adsorption conditions with an adsorbent comprising an X or Y-type zeolite cation exchanged with a cation in the group Fe, Mn, Co, Ni or Zn, thereby selectively adsorbing the p-toluidine thereon. The remainder of the feed mixture is then removed from the adsorbent and the p-toluidine recovered by desorption at desorption conditions with a desorbent material comprising aniline or an alkyl amine excluding alkyl amines having eight or more carbon atoms per molecule when the adsorbent comprises an X-type zeolite.

Other embodiments of our invention encompass details about feed mixtures, adsorbents, desorbent materials and operating conditions, all of which are hereinafter disclosed in the following discussion of each of the facets of the present invention.

DESCRIPTION OF THE INVENTION

At the outset the definitions of various terms used throughout the specification will be useful in making clear the operation, objects and advantages of our process.

A "feed mixture" is a mixture containing one or more extract components and one or more raffinate components to be separated by our process. The term "feed stream" indicates a stream of a feed mixture which passes to the adsorbent used in the process.

An "extract component" is a compound or type of compound that is more selectively adsorbed by the adsorbent while a "raffinate component" is a compound or type of compound that is less selectively adsorbed. In the process, para-toluidine is an extract component and ortho and meta toluidine are rafinate components. The term "desorbent material" shall mean generally a material capable of desorbing an extract component. The term "desorbent stream" or "desorbent input stream" indicates the stream through which desorbent material passes to the adsorbent. The term "raffinate stream" or "raffinate output stream" means a steam through which a raffinate component is removed from the adsorbent. The composition of the raffinate stream can vary from essentially 100% desorbent material to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. At least a portion of the extract stream and preferably at least a portion of the raffinate stream from the separation process are passed to separation means, typically fractionators, where at least a portion of desorbent material is separated to produce an extract product and a raffinate product. The terms "extract product" and "raffinate product" mean products by the process containing, respectively, an extract component and a raffinate component in higher concentrations than those found in the extract stream and the raffinate stream. Although it is possible by the process of this invention to produce a high purity product at high recoveries, it will be appreciated that an extract component is never completely adsorbed by the adsorbent, nor is a raffinate component completely nonadsorbed by the adsorbent. Therefore, varying amounts of a raffinate component can appear in the extract stream and, likewise, varying amounts of an extract component can appear in the raffinate stream. The extract and raffinate streams then are further distinguished from each other and from the feed mixture by the ratio of the concentrations of an extract component and a raffinate component appearing in the particular stream. More specifically, the ratio of the concentration of para-toluidine to that of a less selectively adsorbed ortho and meta toluidine will be lowest in the raffinate stream, next highest in the feed mixture, and the highest in the extract stream. Likewise, the ratio of the concentration of less selectively adsorbed ortho and meta toluidine to that of more selectively adsorbed para-toluidine will be highest in the raffinate stream, next highest in the feed mixture, and the lowest in the extract stream.

The term "selective pore volume" of the adsorbent is defined as the volume of the adsorbent which selectively adsorbs an extract component from the feed mixture. The term "non-selective void volume" of the adsorbent is the volume of the adsorbent which does not selectively retain an extract component from the feed mixture. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into an operational zone for efficient operations to take place for a given quantity of adsorbent. When adsorbent "passes" into an operational zone (hereinafter defined and described) employed in one embodiment of this process, its non-selective void volume together with its selective pore volume carries fluid into that zone. The non-selective void volume is utilized in determining the amount of fluid which should pass into the same zone in a countercurrent direction to the adsorbent to displace the fluid present in the non-selective void volume. If the fluid flow rate passing into a zone is smaller than the non-selective void volume rate of adsorbent material passing into that zone, there is a net entrainment of liquid into the zone by the adsorbent. Since this net entrainment is a fluid present in the non-selective void volume of the adsorbent, it in most instances comprises less selectively retained feed components. The selective pore volume of an adsorbent can in certain instances adsorb portions of raffinate material from the fluid surrounding the adsorbent since in certain instances there is competition between extract material and raffinate material for adsorptive sites within the selective pore volume. If a large quantity of raffinate material with respect to extract material surround the adsorbent, raffinate material can be competitive enough to be adsorbed by the adsorbent.

Chemically, toluidine is a di-substituted benzene. The substituted groups are amino and methyl. The ortho, meta and para isomers of toluidine thus have the following structures:

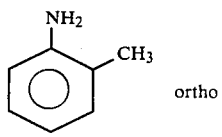
ortho

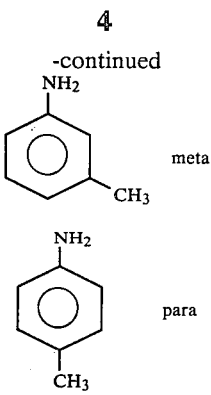
meta para

The prior art has recognized that certain characteristics of adsorbents are highly desirable, if not absolutely necessary, to the successful operation of a selective adsorption process. Such characteristics are equally important to this process. Among such characteristics are: adsorptive capacity for some volume of an extract component per volume of adsorbent; the selective adsorption of an extract component with respect to a raffinate component and the desorbent material; and sufficiently fast rates of adsorption and desorption of an extract component to and from the adsorbent. Capacity of the adsorbent for adsorbing a specific volume of an extract component is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate an extract component of known concentration contained in a particular charge rate of feed mixture. A reduction in the amount of adsorbent required for a specific adsorptive separation reduces the cost of a separation process. It is important that the good initial capacity of the adsorbent be maintained during actual use in the separation process over some economically desirable life. The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another but can also be expressed between any feed mixture component and the desorbent material. The selectivity, (B), is defined as the ratio of the two components of the adsorbed phase over the ratio of the same two components in the unadsorbed phase at equilibrium conditions. Relative selectivity is shown as Equation 1, below:

$$\text{Selectivity} = (B) = \frac{[\text{vol. percent } C/\text{vol. percent } D]_A}{[\text{vol. percent } C/\text{vol. percent } D]_U} \quad \text{Equation 1}$$

where C and D are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases. Where selectivity of two components approaches 1.0, there is preferential adsorption of one component by the adsorbent with respect to the other; they are both adsorbed (or non-adsorbed) to about the same degree with respect to each other. As the (B) becomes less than or greater than 1.0, there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally, desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is just slightly greater than 1.0, it is preferred that such selectivity be reasonably greater than 1.0. Like relative volatility, the higher the selectivity the easier the separation is to perform. Higher selectivities permit a smaller amount of adsorbent to be used. The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

Adsorbents to be used in the process of this invention will comprise specific crystalline aluminosilicates. Particular crystalline aluminosilicates encompassed by the present invention include crystalline aluminosilicate cage structures in which the alumina and silica tetrahedra are initmately connected in an open three dimensional network to form cage-like structures with windowlike pores of about 8 Å free diameter. The tetrahedra are crosslinked by the sharing of oxygen atoms with spaces between the tetrahedra occupied by water molecules prior to partial or total dehydration of this zeolite. The dehydration of the zeolite results in crystals interlaced with cells having molecular dimensions and thus the crystalline aluminosilicates are often referred to as "molecular sieves," particularly when the separation which they effect is dependent essentially upon differences between the sizes of the feed molecules as, for instance, when smaller normal paraffin molecules are separated from larger isoparaffin molecules by using a particular molecular sieve.

In hydrated form, the crystalline aluminosilicates used in the process of this invention generally encompass those zeolites represented by the Formula 1 below:

Formula 1

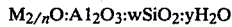

where "M" is a cation which balances the electrovalence of the aluminum-centered tetrahedra and which is generally referred to as an exchangeable cationic site, "n" represents the valence of the cation, "w" represents the moles of SiO$_2$, and "y" represents the moles of water. The generalized cation "M" may be monovalent, divalent or trivalent or mixtures thereof.

The prior art has generally recognized that adsorbents comprising X and Y zeolites can be used in certain adsorptive separation processes. These zeolites are described and defined in U.S. Pat. Nos. 2,882,244 and 3,130,007, respectively incorporated herein by reference thereto. The X zeolite in the hydrated or partially hydrated form can be represented in terms of mole oxides as shown in Formula 2 below:

Formula 2

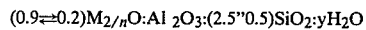

where "M" represents at least one cation having a valence of not more than 3, "n" represents the valence of "M", and "y" is a value up to about 9 depending upon the identity of "M" and the degree of hydration of the crystal. As noted from Formula 2, the SiO$_2$/Al$_2$O$_3$ mole ratio of X zeolite is 2.5±0.5. The cation "M" may be one or more of a number of cations such as a hydrogen cation, an alkali metal cation, or an alkaline earth cation, or other selected cations, and is generally referred to as an exchangeable cationic site. As the X zeolite is initially prepared, the cation "M" is usually predominately sodium, that is, the major cation at the exchangeable cationic sites is sodium and the zeolite is therefore referred to as a sodium-X zeolite. Depending upon the purity of the reactants used to make the zeolite, other cations mentioned above may be present, however, as impurities. The Y zeolite in the hydrated or partially hydrated form can be similarly represented in the terms of mole oxides as in Formula 3 below:

Formula 3

where "M" is at least one cation having a valence not more than 3, "n" represents the valence of "M", "w" is a value greater than about 3 up to about 6, and "y" is a value up to about 9 depending upon the identity of "M" and the degrees of hydration of the crystal. The SiO$_2$/Al$_2$O$_3$ mole ratio for Y zeolites can thus be from about 3 to about 6. Like the X zeolite, the cation "M" may be one or more of a variety of cations but, as the Y zeolite is initially prepared, the cation "M"0 is also usually predominately sodium. A Y zeolite containing predominately sodium cations at the exchangeable cationic sites is therefore referred to as a sodium-Y zeolite.

Cations occupying exchangeable cationic sites in the zeolite may be replaced with other cations by ion exchange methods well-known to those having ordinary skill in the field of crystalline aluminosilicates. Such methods are generally performed by contacting the zeolite or an adsorbent material containing the zeolite with an aqueous solution of the soluble salt of the cation or cations desired to be placed upon the zeolite. After the desired degree of exchange takes place, the sieves are removed from the aqueous solution, washed, and dried to a desired water content. By such methods the sodium cations and any non-sodium cations which might be occupying exchangeable sites as impurities in a sodium X or sodium-Y zeolite can be partially or essentially completely replaced with other cations. The zeolite used in the process of this invention contains cations at exchangeable cationic sites selected from the group of transition metals Fe, Mn, Ni and/or Zn.

Typically, adsorbents used in separative processes contain zeolite crystals dispersed in an amorphous material or inorganic matrix. The zeolite will typically be present in the adsorbent in amounts ranging from about 75 to about 98 wt. % based on volatile-free composition. Volatile-free compositions are generally determined after the adsorbent has been calcined at 900° C. in order to drive off all volatile matter. The remainder of the adsorbent will generally be the inorganic matrix material such as silica, titania, or alumina or mixtures thereof, or compounds, such as clays, which material is present in intimate mixture with the small particles of the zeolite material. This matrix material may be an adjunct of the manufacturing process for zeolite (for example, intentionally incomplete purification of either zeolite during its manufacture) or it may be added to relatively pure zeolite, but in either case its usual purpose is as a binder to aid in forming or agglomerating the hard crystalline particles of the zeolite. Normally, the adsorbent will be in the form of particles such as extrudates, aggregates, tablets, macrospheres or granules having a desired particle size range. The typical adsorbent will have a particle size range of about 16-60 mesh (Standard U.S. Mesh). Examples of zeolites used in adsorbents known to the art, either as is or after cation exchange, are "Molecular Sieves 13X" and "SK-40" both of which are available from the Linde Company, Tonawanda, New York. The first material of course contains X zeolite while the latter material contains Y zeolite.

The separation of the isomers of toluidine on transition metal exchanged X and Y zeolites is based on the chemical interaction between the amino group of the toluidine molecule and the transition metal ions bound to the zeolite framework. In particular, it is well-known that complexes can be formed from amines and transition metals in which the electron lone pair situated on the nitrogen atom of the amine functionality is donated to the metal ion, resulting in a Lewis acid-Lewis base adduct. In the case of the present adsorptive separation, such adducts are formed between the transition metal ions exchanged onto the zeolite and the amino functionality of all three isomers, ortho, meta, and para toluidine. However, because the position of the amino and methyl group on the aromatic ring relative to one another differs for the three isomers, the steric component for this coordination is also different. This is espeically so for the ortho isomer, where the amino and methyl group are adjacent on the ring; consequently, the coordination of ortho-toluidine to a transition metal ion on a zeolite is sterically more hindered relative to meta and para, with the result that in the separation process the ortho isomer is the least strongly adsorbed of the three isomers. In this manner a complexive separation process results. The effect of desorbent is manifested in that the meta and para isomers may be retained to different extents with different desorbents, but the ortho isomer is always observed to be least strongly adsorbed.

Desorbent materials used in various prior art adsorptive separation processes vary depending upon such factors as the type of operation employed. In the swing bed system in which the selectively adsorbed feed component is removed from the adsorbent by a purge stream desorbent, selection is not as critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which are generally operated continuously at substantially constant pressures and temperatures to insure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity (hereinafter discussed in more detail), it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for an extract component with respect to a raffinate component. Desorbent materials should additionally be substances which are easily separable from the feed mixture that is passed into the process. Both the raffinate stream and the extract stream are removed from the adsorbent in admixture with desorbent material and without a method of separating at least a portion of the desorbent material, the purity of the extract product and the raffinate product would not be very high nor would the desorbent material be available for reuse in the process. It is therefore contemplated that any desorbent material used in this process will preferably have a substantially different average boiling point than that of the feed mixture to allow separation of at least a portion of desorbent material from feed components in the extract and raffinate streams by simple fractional distillation, thereby permitting reuse of desorbent material in the process. The term "substantially different" as used herein shall mean that the difference between the average boiling points between the desorbent material and the feed mixture shall be at least about 5° C. The boiling range of the desorbent material may be higher or lower than that of the feed mixture. Finally, desorbent materials should also be materials which are readily available and therefore reasonable in cost. In the preferred isothermal, isobaric, liquid-phase operation of the process of our invention, we have found that desorbent material comprising aniline or an alkyl amine, excluding alkyl amines having eight or more carbon atoms per molecule when the adsorbent comprises an X-type zeolite, will result in selectivity for the paraisomer when used with the above discussed adsorbent.

The adsorbent may be employed in the form of a dense compact fixed bed which is alternatively contacted with the feed mixture and desorbent materials. In the simplest embodiment of the invention, the adsorbent is employed in the form of a single static bed in which case the process is only semi-continuous. In another embodiment, a set of two or more static beds may be employed in fixed bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Moving bed or simulated moving bed flow systems, however, have a mush greater separation efficiency than fixed bed systems and are therefore preferred. In the moving bed or simulated moving bed processes, the retention and displacement operations are continuously taking place which allows both continuous production of an extract and a raffinate stream and the continual use of feed and displacement fluid streams. One preferred embodiment of this process utilizes what is known in the art as the simulated moving bed countercurrent flow system. The operating principles and sequence of such a flow system are described in U.S. Pat. No. 2,985,589, incorporated herein by reference. In such a system, it is the progressive movement of multiple liquid access points down a molecular sieve chamber that simulates the upward movement of molecular sieve contained in the chamber. Reference can also be made to D. B. Broughton U.S. Pat. No. 2,985,589 and to a paper entitled, "Continuous Adsorptive Processing—A new Separation Technique" by D. B. Broughton presented at the 34th Annual Meeting of the Society of Chemical Engineers at Tokyo, Japan on Apr. 2, 1969, both references incorporated herein by reference, for further explanation of the simulated moving bed countercurrent process flow scheme.

Another embodiment of a simulated moving bed flow system suitable for use in the process of the present invention is the cocurrent high efficiency simulated moving bed process disclosed in our assignee's U.S. Pat. No. 4,402,832, incorporated by reference herein in its entirety.

It is contemplated with any flow scheme used to carry out the present invention that at least a portion of the extract output stream will pass into a separation means wherein at least a portion of the desorbent material can be separated to produce an extract product containing a reduced concentration of desorbent material. Preferably, but not necessary to the operation of the process, at least a portion of the raffinate output stream will also be passed to a separation means wherein at least a portion of the desorbent material can be separated to produce a desorbent material steam which can be reused in the process and a raffinate product containing a reduced concentration of desorbent material. The separation means will typically be a fractionation column, the design and operation of which is well-known to the separation art.

Although both liquid and vapor phase operations can be used in many absorptive separation processes, liquid-phase operation is preferred for this process because of the lower temperature requirements and because of the higher yields of extract product that can be obtained with liquid-phase operation over those obtained with vapor-phase operation. Desorption conditions will thus include, as hereinbefore mentioned, a pressure sufficient to maintain liquidphase. Adsorption conditions will include the same range of temperatures and pressures as used for desorption conditions.

A dynamic testing apparatus is employed to test various adsorbents with a particular feed mixture and desorbent material to measure the adsorption characteristics of retention capacity and exchange rate. The apparatus consists of a helical adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters adn chromatographs can be attached to the outlet line of the chamber and used to detect quantitatively or determine qualitatively one or more components in the effluent stream leaving the adsorbent chamber. A pulse test, performed using this apparatus and the following general procedure, is used to determine data for various adsorbent systems. The adsorbent is filled to equilibrium with a particular desorbent material by passing the desorbent material through the adsorbent chamber. At a convenient time, a pulse of feed containing known concentrations of a tracer and of a particular extract component or of a raffinate component or both, all diluted in desorbent material is injected for a duration of several minutes. Desorbent material flow is resumed, and the tracer and the extract component or the raffinate component (or both) are eluted as in a liquid-solid chromatographic operation. The effluent can be analyzed on-stream or alternatively, effluent samples can be collected periodically and later analyzed separately by analytical equipment and traces of the envelopes or corresponding component peaks developed.

From information derived from the test, adsorbent performance can be rated in terms of void volume, retention volume for an extract or a raffinate component, and the rate of desorption of an extract component from the adsorbent. The retention volume of an extract or a raffinate component may be characterized by the distance between the center of the peak envelope of the tracer component or some other known reference point. It is expressed in terms of the volume in cubic centimeters of desorbent material pumped during this time interval represented by the distance between the peak envelopes. The rate of exchange of an extract component with the desorbent material can generally be characterized by the width of the peak envelopes at half intensity. The narrower the peak width, the faster the desorption rate. The desorption rate can also be characterized by the distance between the center of the tracer peak envelope and the disappearance of an extract component which has just been desorbed. This distance is again the volume of desorbent material pumped during this time interval.

The following non-limiting example is presented to illustrate the process of the present invention and is not intended to unduly restrict the scope of the claims attached hereto.

EXAMPLE

The above described pulse test apparatus was used to obtain data for this example in a series of eight test runs. The liquid temperature was 150° C. and the flow was up the column at the rate of 1.2 ml/min. The feed stream comprised 2.6 cc pulses of a solution containing 0.5 gm of each of the toluidine isomers, and 0.5 gm of n-$C_{14}$ tracer, all dissolved in 3 gm of desorbent. The column was packed with clay bound adsorbent of 20-40 mesh particle size.

The results of this example are shown on the following Table:

TABLE

| Run | Adsorbent | $B_{p/o}$ | $B_{p/m}$ | $B_{m/o}$ | Analysis of Metal Content, Wt. % | | Desorbent |
|---|---|---|---|---|---|---|---|
| 1 | Ni X | 2.41 | 1.29 | 2.10 | 7.03 Ni | 6.92 Na | 15% aniline/toluene |
| 2 | Ni Y | 2.48 | 1.27 | 1.95 | 4.79 Ni | 4.28 Na | 15% aniline/toluene |
| 3 | Ni Y | 2.54 | 1.17 | 2.17 | 7.47 Ni | 2.47 Na | 15% aniline/toluene |
| 4 | Ni Y | 1.96 | 1.36 | 1.44 | 4.79 Ni | 4.28 Na | 15% n-butylamine/toluene |
| 5 | Co Y | 2.84 | 1.28 | 2.21 | 6.50 Co | 3.66 Na | 15% aniline/toluene |
| 6 | Ni X | 1.80 | $B_{m/p} = 1.30$ | 2.32 | 7.03 Ni | 6.92 Na | 15% n-octylamine/toluene |
| 7 | Ni X | 1.29 | $B_{m/p} = 1.38$ | 1.78 | 7.03 Ni | 6.92 Na | 50% n-propanol/toluene |
| 8 | Na Y | 1.37 | 1.20 | 1.14 | — | — | 15% aniline/toluene |

It may be noted from the above that for test runs 6 and 7, which did not utilize the desorbent required by the present invention, the system was meta selective. In run 8, which did not use an adsorbent required by the present invention, the selectivities for the para-isomer, both with regard to the meta and ortho isomers, were so low as to be ineffective.

In general, the above data does show that the present invention provides a para-toluidine selective system. Although the selectivities for the para to meta isomers are not as high as what is usually desired, the present invention is considered to have sufficient utility for the separation of interest. It is furthermore contemplated that the typical feedstock for use in the process of the present invention will be so low in meta content (3-4 LVA% of the three toluidine isomers) that the low para to meta selectivity would not cause a significant problem.

What is claimed is:

1. A process for separating p-toluidine by adsorption of said p-toluidine in the pores of a hereinafter characterized X or Y-type zeolite from a feed mixture comprising p-toluidine and o-toluidine or m-toluidine said process comprising contacting said mixture with an adsorbent comprising an X or Y-type zeolite having cations exchanged with a cation selected from the group consisting of Fe, Mn, Co, Ni and Zn at conditions of from about 20° C. to about 200° C. and a pressure sufficient to maintain said liquid phase to selectively adsorb said p-toluidine while said o-toluidine or m-toluidine are removed from said adsorbent, and thereafter contacting said X or Y-type zeolite containing said p-toluidine with a desorbent, at desorption conditions, to remove said adsorbed p-toluidine derived from said feed mixture, said desorbent material comprising aniline or an alkyl amine, excluding alkylamines having eight or more carbon atoms per molecule when said adsorbent comprises an X-type zeolite.

2. The process of claim 1 wherein the boiling range of said desorbent material is at least about 5° C. higher or lower than that of the feed mixture.

3. The process of claim 1 wherein said desorption conditions include a temperature within the range of from about 20° C. to about 200° C. and a pressure sufficient to maintain liquid phase.

4. The process of claim 1 wherein said process is effected with a simulated moving bed flow system.

5. The process of claim 1 wherein said process is effected with a static bed system.

6. A process for separating p-toluidine by adsorption of said p-toluidine in the pores of a hereinafter characterized X or Y-type zeolite from a feed mixture comprising p-toluidine o-toluidine and m-toluidine said process comprising contacting said mixture with an adsorbent comprising an X or Y-type zeolite having cations exchanged with a cation selected from the group consisting of Fe, Mn, Co, Ni and Zn at conditions of from about 20° C. to about 200° C. and a pressure sufficient to maintain said liquid phase to selectively adsorb said p-toluidine while said o-toluidine and m-toluidine are removed from said adsorbent, and thereafter contacting said X or Y-type zeolite containing said p-toluidine with a desorbent, at desorption conditions, to remove said adsorbed p-toluidine derived from said feed mixture, said desorbent material containing aniline or an alkyl amine excluding alkylamines having eight or more carbon atoms per molecule when said adsorbent comprises an X-type zeolite.

* * * * *